United States Patent
Shalev et al.

(10) Patent No.: US 10,271,489 B2
(45) Date of Patent: Apr. 30, 2019

(54) PRODUCTION OF HYBRID SEEDS LOT USING NATURAL POLLINATION

(71) Applicant: EQUI-nom Ltd., Kibbutz Givat Brenner (IL)

(72) Inventors: Gil Shalev, Ramot Mehir (IL); Oron Gar, Kibbutz Sde Yoav (IL)

(73) Assignee: EQUI-NOM LTD., Kibbutz Givat Brenner (IL)

( * ) Notice: Subject to any disclaimer, the term of this patent is extended or adjusted under 35 U.S.C. 154(b) by 18 days.

(21) Appl. No.: 15/323,969

(22) PCT Filed: Oct. 27, 2015

(86) PCT No.: PCT/IL2015/051049
§ 371 (c)(1),
(2) Date: Jan. 5, 2017

(87) PCT Pub. No.: WO2016/067284
PCT Pub. Date: May 6, 2016

(65) Prior Publication Data
US 2017/0196188 A1    Jul. 13, 2017

Related U.S. Application Data

(60) Provisional application No. 62/069,341, filed on Oct. 28, 2014.

(30) Foreign Application Priority Data

Jun. 29, 2015    (IL) .......................................... 239702

(51) Int. Cl.
*A01H 5/10* (2018.01)
*A01H 1/02* (2006.01)
*A01H 1/04* (2006.01)

(52) U.S. Cl.
CPC .............. *A01H 5/10* (2013.01); *A01H 1/02* (2013.01); *A01H 1/04* (2013.01)

(58) Field of Classification Search
None
See application file for complete search history.

(56) References Cited

U.S. PATENT DOCUMENTS

| | | |
|---|---|---|
| 3,903,645 A | 9/1975 | Bradner |
| 4,077,157 A | 3/1978 | Bradner |
| 5,038,518 A | 8/1991 | Davis |
| 6,100,452 A | 8/2000 | Langham |
| 8,080,707 B2 | 12/2011 | Langham |
| 8,502,019 B2 | 8/2013 | Sun |
| 8,507,750 B1 | 8/2013 | Langham |
| 8,581,028 B2 | 11/2013 | Langham |
| 8,664,472 B2 | 3/2014 | Langham |
| 9,125,372 B1 | 9/2015 | Langham |
| 2006/0277618 A1 | 12/2006 | Sun |
| 2011/0232247 A1 | 9/2011 | Zhu et al. |
| 2011/0312022 A1 | 12/2011 | Gardner |
| 2013/0167496 A1 | 7/2013 | Bensley-Bromilow et al. |
| 2015/0264879 A1 | 9/2015 | Langham |
| 2015/0264880 A1 | 9/2015 | Langham |

OTHER PUBLICATIONS

Bakheit et al. Assiut Journal of Agricultural Sciences 27(4): 27-40 (1996).*
Linum genus description from Wikipedia, accessed Dec. 4, 2018.*
Roach et al., "Maternal Effects in Plants", Annual Review of Ecology and Systematics, vol. 18 (1987), pp. 209-235.
Harper et al., "The Shapes and Sizes of Seeds", Annu. Rev. Ecol. Syst. 1970.1:327-356.
International Search Report of Application No. PCT/IL2015/051049 dated Jan. 31, 2016.
Shi et al. 1996, Analysis of genetic effects on nutrient quality traits in *indica* rice, Theoretical and Applied Genetics, 92(8): 1099-1102.
Panthee et al. 2005, Quantitative Trait Loci for Seed Protein and Oil Concentration, and Seed Size in Soybean, Crop Sci. 45:2015-2022.
Sanjib Nandy, et al, 2009, Inheritance of Grain Color Controlling Genes in Diverse Wheat Crosses Using Near-infrared Spectroscopy, Int'l Jrnl. of Plant Breeding, 3 (1): 52-57.
Jondhale et al. 2015, Inheritance of Grain Size and Shape in Rice (*Oryza sativa* L.). Periodic Research. IV. 47-49.

\* cited by examiner

*Primary Examiner* — David T Fox
(74) *Attorney, Agent, or Firm* — Pearl Cohen Zedek Latzer Baratz LLP

(57) ABSTRACT

Methods and hybrid seed are provided which involve growing two varieties of a field crop which is at least partially cross-pollinated in the field, wherein the two varieties are fertile with respect to both male and female functions, are selected to yield specified hybrid(s), and are distinguishable with respect to seed characteristic(s). Collected seed from the grown field crop are separated into fractions with respect to the seed characteristic, wherein at least one fraction is of hybrid seeds of the specified hybrid(s). For example, the separated fraction may be intermediate with respect to the seed characteristic(s) between seed fractions of the non-hybridized two varieties. Respective varieties may be bred to yield hybrids with required traits, which are distinguishable from the parent varieties through seed characteristic(s) such as size, weight or optical parameters that enable sorting out the hybrids from the overall crop.

12 Claims, 10 Drawing Sheets

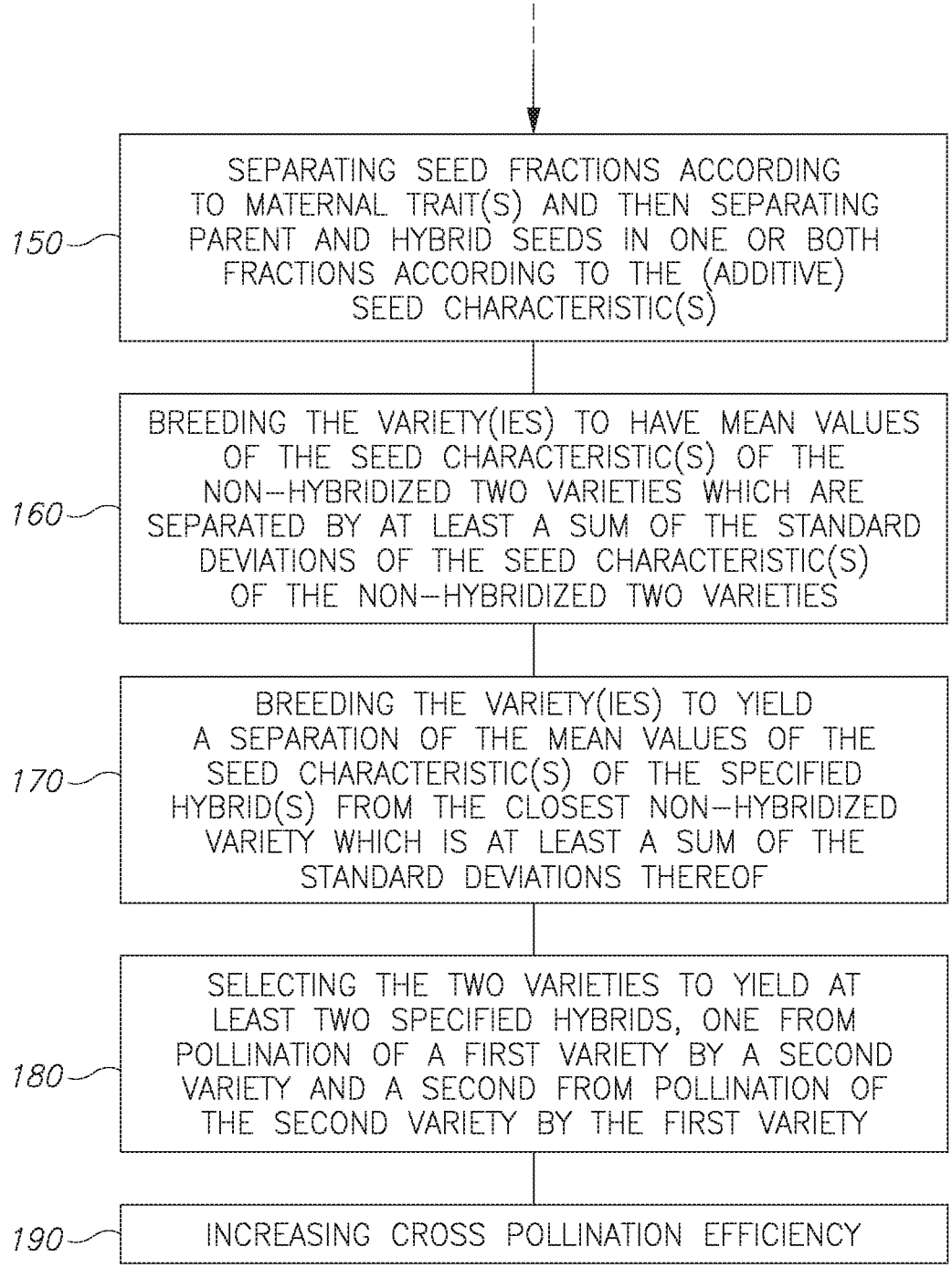
Figure 2 (cont. 1)

|  | Maternal parent I ($n_I$ genome) | | Maternal parent II ($n_{II}$ genome) | |
|---|---|---|---|---|
|  | endosperm | embryo | endosperm | embryo |
| Paternal parent I ($n_I$ genome) | $3n_I$ | $2n_I$ | $1n_I+2n_{II}$ | $1n_I+1n_{II}$ |
|  | Variety 1 | | Hybrid 2 | |
| Paternal parent II ($n_{II}$ genome) | $2n_I+1n_{II}$ | $1n_I+1n_{II}$ | $3n_{II}$ | $2n_{II}$ |
|  | Hybrid 1 | | Variety 2 | |

Figure 7

| TGW (gr) | | Male | | | | | | | | | |
|---|---|---|---|---|---|---|---|---|---|---|---|
| SD (gr) | | P1 | P2 | P3 | P4 | P5 | P6 | P7 | P8 | P9 | P10 |
| Female | P1 | 5.20<br>*0.10* | 5.19<br>*0.01* | 5.16<br>*0.02* | 5.10<br>*0.06* | 5.05<br>*0.09* | 4.20<br>*0.05* | 4.20<br>*0.16* | 3.98<br>*0.28* | 3.80<br>*0.21* | 3.50<br>*0.05* |
| | P2 | 5.19<br>*0.01* | 5.18<br>*0.04* | 5.16<br>*0.05* | 5.05<br>*0.10* | 5.00<br>*0.15* | 4.20<br>*0.03* | 4.00<br>*0.15* | 3.50<br>*0.30* | 3.80<br>*0.22* | 3.80<br>*0.05* |
| | P3 | 5.16<br>*0.02* | 5.16<br>*0.08* | 5.14<br>*0.07* | 5.07<br>*0.90* | 5.00<br>*0.05* | 4.15<br>*0.10* | 4.00<br>*0.15* | 4.20<br>*0.30* | 4.20<br>*0.20* | 4.20<br>*0.03* |
| | P4 | 5.02<br>*0.02* | 5.01<br>*0.08* | 4.99<br>*0.10* | 4.98<br>*0.06* | 4.95<br>*0.03* | 4.10<br>*0.05* | 4.05<br>*0.10* | 4.10<br>*0.22* | 3.60<br>*0.18* | 3.60<br>*0.07* |
| | P5 | 5.00<br>*0.10* | 4.97<br>*0.12* | 4.97<br>*0.10* | 4.96<br>*0.08* | 4.95<br>*0.04* | 4.05<br>*0.08* | 3.60<br>*0.09* | 3.50<br>*0.15* | 3.20<br>*0.15* | 3.30<br>*0.03* |
| | P6 | 3.31<br>*0.43* | 3.29<br>*0.04* | 3.20<br>*0.11* | 3.15<br>*0.08* | 3.20<br>*0.15* | 2.19<br>*0.04* | 2.15<br>*0.04* | 2.12<br>*0.05* | 2.09<br>*0.09* | 2.10<br>*0.10* |
| | P7 | 3.20<br>*0.25* | 3.15<br>*0.05* | 3.20<br>*0.09* | 3.10<br>*0.11* | 3.00<br>*0.16* | 2.13<br>*0.06* | 2.12<br>*0.04* | 2.10<br>*0.05* | 2.09<br>*0.03* | 2.05<br>*0.08* |
| | P8 | 3.20<br>*0.44* | 3.20<br>*0.07* | 3.05<br>*0.13* | 3.03<br>*0.09* | 3.00<br>*0.14* | 2.08<br>*0.05* | 2.08<br>*0.04* | 2.08<br>*0.04* | 2.05<br>*0.15* | 2.02<br>*0.10* |
| | P9 | 3.15<br>*0.48* | 3.11<br>*0.03* | 3.09<br>*0.15* | 3.07<br>*0.07* | 2.99<br>*0.12* | 2.03<br>*0.07* | 2.02<br>*0.06* | 2.01<br>*0.02* | 2.00<br>*0.01* | 2.40<br>*0.03* |
| | P10 | 3.15<br>*0.40* | 3.10<br>*0.09* | 2.98<br>*0.09* | 2.96<br>*0.08* | 2.95<br>*0.16* | 2.00<br>*0.03* | 1.99<br>*0.02* | 1.98<br>*0.03* | 2.20<br>*0.02* | 1.96<br>*0.04* |

Figure 8

PRODUCTION OF HYBRID SEEDS LOT USING NATURAL POLLINATION

CROSS REFERENCE TO RELATED APPLICATIONS

This application is a National Phase Application of PCT International Application No. PCT/IL2015/051049, International Filing Date Oct. 27, 2015, claiming priority of U.S. Provisional Patent Application No. 62/069,341 filed on Oct. 28, 2014 and of Israeli Patent Application No. 239702 filed on Jun. 29, 2015, which are incorporated herein by reference in their respective entirety.

BACKGROUND OF THE INVENTION

1. Technical Field

The present invention relates to the field of hybrid production methods in plants, and more particularly, to hybrid production using natural pollination.

2. Discussion of Related Art

The term "heterosis" describes the genetic phenomenon in which a hybrid exhibits an increased function of one or more biological qualities, beyond the respective quality in its parents. Heterosis has been long utilized in plant breeding as it provides several agronomic advantages for the offspring over the parental lines such as higher yield and environmental stability.

A seed is an embryonic plant enclosed in a protective coating. It is the product of the ripened ovule which develops after fertilization. The seed consists of, from the outer to the inner parts, the testa (coating), the pericarp, the endosperm and the embryo.

Pollination is the process by which pollen is transferred from the anther (male part) to the stigma (female part) of the plant, thereby enabling fertilization and reproduction. The pollen grain (gametophyte) containing the male gametes are naturally transported to the stigma by biotic vectors (like insects, animals) and/or by abiotic vectors (like wind, water), where it germinates and its pollen tube grows down the style to the ovary. The two gametes in the pollen grain travel down the tube to where the gametophyte(s) containing the female gametes are held within the carpel. One nucleus fuses with the polar bodies to produce the endosperm tissues, and the other with the ovule to produce the embryo.

Pollination can be accomplished by cross-pollination, also called allogamy, which occurs only when pollen is delivered to a flower from a different plant, or by self-pollination, also called autogamy or geitonogamy, which occurs when pollen from one flower pollinates the same flower or other flowers of the same individual, respectively.

Unlike the embryo, which contain two nuclei (the maternal nucleus and the paternal nucleus), the endosperm is formed by multiple fertilizations, which usually result in 3N endosperm with two nuclei from the maternal parent and only one from the paternal parent. Although the endosperm is not always triploid, it always contains more maternal genes than paternal genes. Maternal and paternal effects in seed originate via the endosperm. As a consequence of the differential dosage of male and female genes on the endosperm, differences in seed characteristic are occurring in size, shape, color, weight, enzymes contents, proteins contents, nutrition contents and metabolite contents. The female parent may have a more important role in determining seed characteristics, as reviewed in D. A. Roach and R. D. Wulff 1987, Maternal effects in plants, Annual review of ecology and systematics 18:209-235.

The genetic regulation of seed size is a complicated matter because one paternal genome contribution and at least two maternal genome contributions determine the endosperm genetics, whereas the genomic contribution to the embryo is equal from both parents. The relative role of maternal and paternal control of seed characteristic might therefore be expected to be largely determined by the relative mass contributed by the three generations represented in the seed, nevertheless, the food supply for the whole unit is entirely maternal. To what degree seed size is determined by the forces of supply from the parent and by the forces of demand from the developing embryo and endosperm, as overviewed e.g., in J. L. Harper, P. H. Lovell and K. G. Moore 1970, The shapes and sizes of seeds, Annual review of ecology and systematics 1:327-356, is an interesting and still largely open question, Current hybrid production methods utilize different natural and artificial barriers to prevent self-pollination. For example, such barriers include dioecious flower anatomy, self-incompatibility, manual emasculation and genetic or induced male sterility. Without these barriers the harvested seeds lot contains different proportions of four types of seeds: self and cross-pollinated seeds from parent 1 plants and self and cross-pollinated seeds from parent 2 plants. Furthermore, it is not an uncommon experience to realize that the seeds lot cannot be labeled nor marketed as hybrid seeds lot without using such barriers.

U.S. Pat. No. 3,903,645, which is incorporated herein by reference in its entirety, discloses a process for production of seed capable of growing F1 hybrid soybean plants. A substantially uniform first population of atypical soybean plants having exposed floral stigmas and the propensity to yield seed of a small size is grown adjacent to a substantially uniform second population of soybean plants having the propensity to yield seed of a larger size. The soybean plants of the first population are capable of undergoing cross-pollination with the aid of pollen carrying insects as well as self-pollination. Following cross- and self-pollination and seed formation seed selectively is recovered from the plants of the first population, and is segregated based on seed size with the relatively larger seed resulting from the cross-pollination being capable of growing F1 hybrid soybean plants. The plants of the first population additionally exhibit a characteristic wherein the dehiscence of anther tissue to discharge pollen is delayed at least until the florets open, and/or produce less than the normal quantity of viable pollen commonly observed in soybean plants thereby tending to enhance the relative proportion of cross-pollination occurring in the first population.

U.S. Pat. No. 8,502,019, which is incorporated herein by reference in its entirety, discloses a method for increasing production of hybrid seed of bee-pollinated crops, such as alfalfa and soybean at predetermined hybridity levels. Hybrid seed is produced using female and pollenizer plants at a selected ratio of female plants to pollenizer plants. The female plants and the pollenizer plants are intermingled in the hybrid seed's production field. Prediction of percentage of hybridity at various female to pollenizer ratios allows for selection of a ratio of female plants to pollenizer plants to provide seed at a test percentage of hybridity. The percentage of hybridity may be increased post-harvest by employing techniques using seed properties such as size differential, color or density to remove a higher percentage of non-hybrid seed. The hybrid seed product is maximized at various hybridity levels. Planting according to sub-rows allows for separate harvesting of intermingled crops. Testing the hybrid seed product provides verification of percentage of hybridity.

SUMMARY OF THE INVENTION

The following is a simplified summary providing an initial understanding of the invention. The summary does not necessarily identify key elements nor limit the scope of the invention, but merely serves as an introduction to the following description.

One aspect of the present invention provides a method of obtaining specified hybrid seeds, the method comprising growing two varieties of a field crop which is at least partially bi-directionally cross-pollinated in the field, wherein the two varieties: are fertile with respect to both male and female functions, are selected to yield at least one specified hybrid, and are distinguishable with respect to at least one seed characteristic. The method further comprises collecting seed from the grown field crop, and separating, from the collected seed, at least one fraction of hybrid seeds of the at least one specified hybrid, wherein the at least one separated fraction is intermediate, with respect to the at least one seed characteristic, between seed fractions of the non-hybridized two varieties.

These, additional, and/or other aspects and/or advantages of the present invention are set forth in the detailed description that follows; possibly inferable from the detailed description; and/or learnable by practice of the present invention.

BRIEF DESCRIPTION OF THE DRAWINGS

For a better understanding of embodiments of the invention and to show how the same may be carried into effect, reference will now be made, purely by way of example, to the accompanying drawings in which like numerals designate corresponding elements or sections throughout.

In the accompanying drawings:

FIG. 7 is a highly schematic characterization of offspring seeds (each type denoted by a thick border), according to maternal and paternal identities with respect to their inherited genomes ($n_I$ or $n_{II}$) exhibiting different doses (1, 2 or 3) in the resulting diploid seed.

FIG. 8 depicts an example for the crossing stage in the breeding of parental lines for hybrid production in sesame.

DETAILED DESCRIPTION OF THE INVENTION

Figure 1A:
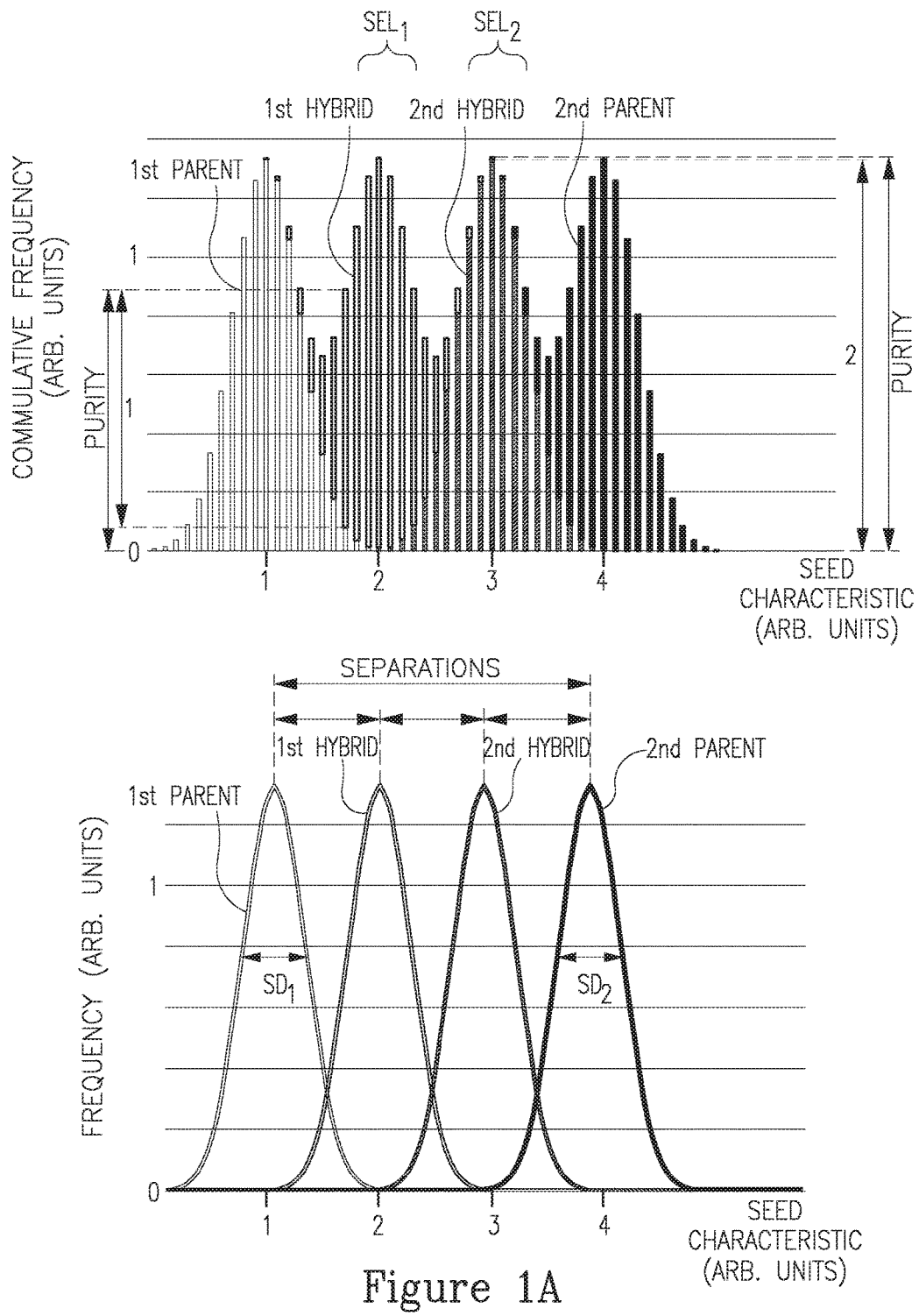
FIGS. 1A and 1B are high-level conceptual illustrations of distributions of a seed characteristic, according to some embodiments of the invention.

Prior to the detailed description being set forth, it may be helpful to set forth definitions of certain terms that will be used hereinafter.

The terms "trait" or "property" as used in this application refer to any feature of a plant or a seed which is selected or bred for, typically as required features of product hybrids. The terms "seed characteristic" or "differentiation characteristic" (DC) as used in this application refer to specific features which are selected or bred for the purpose of separating the hybrid seeds from pure parent seeds and/or from each other. The difference between traits and seed characteristic(s) lies in their respective roles—the former characterizing the final product of hybrids and the latter providing the separation parameter(s) for separating the hybrid seeds from the parents' seeds. Moreover, the terms "trait" or "property" as used in this application refer to features in which parents and hybrids are similar, while the terms "seed characteristic" or "differentiation characteristic" (DC) as used in this application refer to features in which parents and hybrids are different and distinguishable from each other.

The terms "mean value" and "standard deviation" as used in this application refer to corresponding statistical parameters of Gaussian distribution of one or more seed characteristic in a seed population, as well to corresponding statistical parameters in other distribution of seed characteristic(s) in non-Gaussian distributions. For example, the mean values and the standard deviations may be statistical measures of empirical distributions of the respective seeds.

With specific reference now to the drawings in detail, it is stressed that the particulars shown are by way of example and for purposes of illustrative discussion of the preferred embodiments of the present invention only, and are presented in the cause of providing what is believed to be the most useful and readily understood description of the principles and conceptual aspects of the invention. In this regard, no attempt is made to show structural details of the invention in more detail than is necessary for a fundamental understanding of the invention, the description taken with the drawings making apparent to those skilled in the art how the several forms of the invention may be embodied in practice.

Before at least one embodiment of the invention is explained in detail, it is to be understood that the invention is not limited in its application to the details of construction and the arrangement of the components set forth in the following description or illustrated in the drawings. The invention is applicable to other embodiments or of being practiced or carried out in various ways. In addition, it is to be understood that the phraseology and terminology employed herein is for the purpose of description and should not be regarded as limiting.

Provided are a method of production of hybrid seeds lot using natural pollination, as well as corresponding systems and devices involved in the production and separation, and related sowing patterns, selection of parents and resulting seed assemblies with given distribution characteristics. Hybrid seeds are produced using two parents, which are intermingled, in the hybrid seed production field. Applying the developed algorithm enables to exploit the genetic differences in seed characteristics (such as shape, size, color, weight and internal components) between the parents by employing post-harvest techniques to increase the percentage of hybridity. Field trial evaluation for the seeds lot provide verification of the required level of hybridity which allowed its labeling and marketing as hybrid seeds lot.

Certain embodiments overcome the challenge of producing hybrid seed using natural pollination by exploiting or breeding differences in seed characteristics. Genetic differences between the parents in the seed's endosperm and embryo characteristics, such as size, shape, color and metabolic content, are affected by the genetic differences between the parental lines and the epigenetic interaction of the created seed, resulting in different characteristics in the offspring seeds, as illustrated schematically in FIG. 7.

FIG. 7: Highly schematic characterization of offspring seeds (each type denoted by a thick border), according to maternal and paternal identities with respect to their inherited genomes ($n_I$ or $n_{II}$) exhibiting different doses (1, 2 or 3) in the resulting diploid seed.

As is schematically shown in FIG. 7, different combinations of parent plant types result in seed having different genomic constitution in the endosperm and the embryo seed tissues, which result in variety in the offspring seeds. Specifically, the four types of seeds would differ in certain characteristics relating to seed weight or size. It is noted that not only do hybrids differ from the varieties in their genomic composition, but the hybrids also differ among themselves in their genomic composition, as they have namely different endosperm doses of the parent genomes.

Certain embodiments comprise a process of developing hybrid seed based on designing (i.e., selecting or breeding) parental lines with specific genetic variation that increases phenotypic differences in seed characteristics between the two parental lines, to create traceable differences in seed characteristic between the hybrid seeds and the non-hybrid seeds and thus to enable differentiation of the four different seed lots. Certain methods combine breeding the parental lines for specific seed characteristics and seed production uses natural pollination.

It is noted that hybrid seed are usually bred to express a given set of phenotypic characters by selecting parent varieties. For example, hybridization may be used to achieve hybrid vigor (heterosis) in certain characteristics. As some of the plant's characteristics are additive (i.e., progeny's characteristics reflect an average of the respective parent characteristics) while other are heterotic (i.e., progeny's characteristics may be well beyond the respective characteristic of either parent), it is common in hybrid breeding to use parent varieties which are similar in the additive characteristics (to achieve maximal hybrid plant characteristic, e.g., seed size or weight) and different in the heterotic characteristic(s) to reach in the latter heterotic effects. Hence, the parental lines are usually bred to display phenotypic variance in heterotic traits only, leaving them to display uniform phenotypes with respect to additive traits. The presented methods maintain this aspect in the hybrid seed except for one or more additive seed characteristic (seed characteristic(s) relating to additive trait(s)) which is used to separate the hybrid(s) from the parent varieties and possibly from each other. Hence, with respect to the seed characteristic(s) which are used to separate the hybrid(s), breeding or selection take an opposite direction in comparison to breeding or selection of the rest of the phenotypic characters, by aiming at parent varieties which are distant from each other with respect to the specific seed characteristic(s) which are used to separate the hybrid(s) (while being close with respect to other phenotypic characters). In certain embodiments, some reduction in the corresponding additive trait(s) in the hybrid plants (at the F2 generation) may be compensated by the ability to separate hybrid seeds from parent seeds and from each other (at the F1 generation). This point is exemplified schematically below.

Referring again to FIG. 7, it is clear that the differences between the distributions of additive seed characteristics in hybrids and the distributions of these additive seed characteristics in the parents are influenced by the seed structure of the respective crop. For example, crops having seeds with a large embryo with respect to the endosperm are expected to have intermediate hybrid seed distributions which are similar among the two hybrids (in both hybrids, each of the parents influences the seed characteristic equally); while crops having seeds with a large endosperm with respect to the embryo are expected to have intermediate hybrid seed distributions which are distinct from each other, as each would be closer to the respective female parent (in each of the hybrids, the maternal parent influences the seed characteristic approximately twice as strong as the paternal parent).

Methods and hybrid seed are provided which involve growing two varieties of a field crop which is at least partially cross-pollinated in the field, wherein the two varieties are fertile with respect to both male and female functions and the cross-pollination is bi-directional, are selected to yield specified hybrid(s), and are distinguishable with respect to seed characteristic(s). Collected seed from the grown field crop are separated into fractions with respect to the seed characteristic, wherein at least one fraction is of hybrid seeds of the specified hybrid(s). The hybrid seeds may then be sown by farmers to yield hybrid plants with heterotic characteristics. For example, the separated fraction may be intermediate with respect to the seed characteristic(s) between seed fractions of the non-hybridized two varieties. Respective varieties may be bred to yield hybrids with required traits, which are distinguishable from the parent varieties through seed characteristic(s) such as size, weight or optical parameters that enable sorting out the hybrids from the overall crop.

Figure 1B:
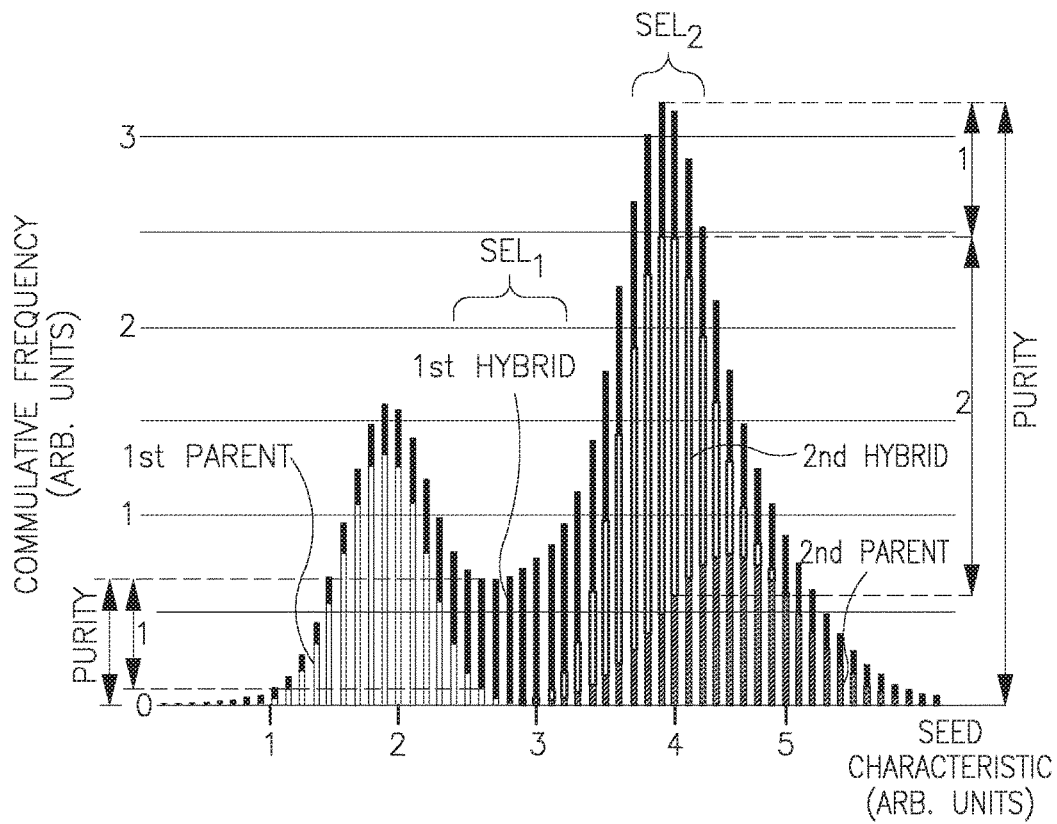
Figure 1B:
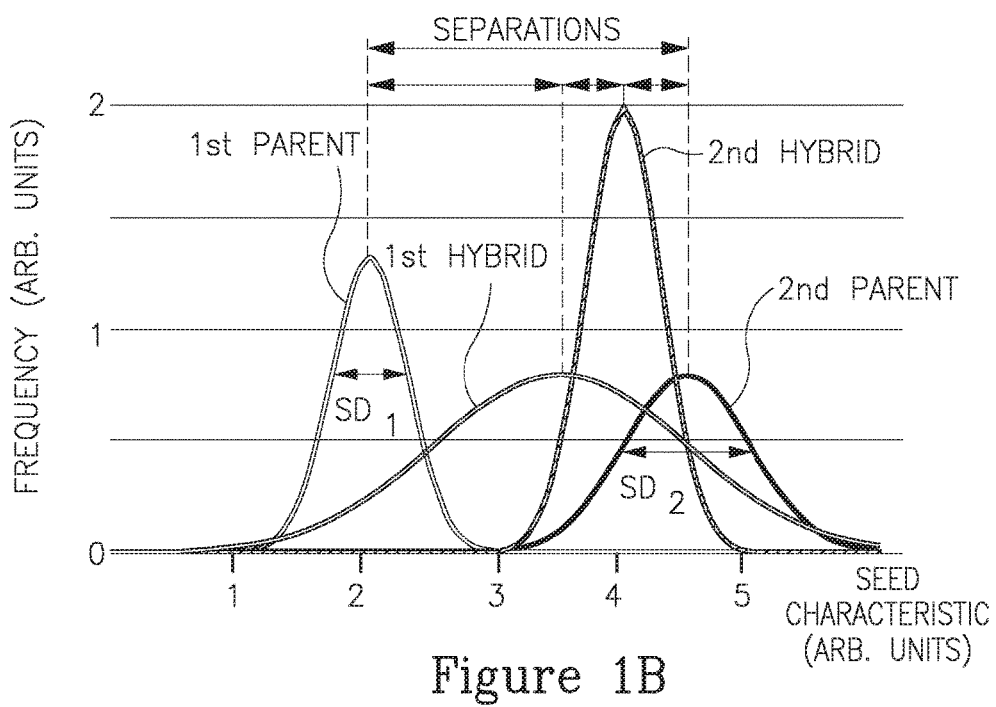

FIGS. 1A and 1B are high-level conceptual illustrations of distributions of a seed characteristic, according to some embodiments of the invention. The illustrations depict two exemplary distributions which may characterize given parent varieties or may be set as breeding targets. The x-axis denotes an abstract seed characteristic (which may represent e.g., a seed size, a seed weight, a visual or an optical characteristic of the seed etc., the units are arbitrary) and the y-axis denotes a frequency of the value of the seed characteristic (in abstract terms and arbitrary units). The bottom diagrams present the distributions of the parents and the hybrids in an overlapping manner, and the top diagrams present the distributions of the parents and the hybrids in a cumulative manner, i.e., the former depicts breeding targets and the latter depicts resulting seed distributions from the produced crops. It is noted that while FIGS. 1A and 1B depict schematically Gaussian distributions, the invention is in no way limited to Gaussian distributions and may be likewise applicable to any theoretical or empirical distribution of seed characteristics, using equivalent calculation of mean values and standard deviations (e.g., with the mean values and the standard deviations being statistical measures of empirical distributions of the respective seeds).

FIG. 1A presents a case of distinct distributions of the seed characteristic, which have little overlap and enable separation of the hybrids according to the seed characteristic with a high purity level. For example, in FIG. 1A, the large majority of seed within the range of ca. 2±0.3 is of the first hybrid and the large majority of seed within the range of ca. 3±0.3 is of the second hybrid. FIG. 1B presents a case of less distinct distributions of the seed characteristic, which have significant overlaps yet nevertheless enable separation of the hybrids according to the seed characteristic. For example, in FIG. 1B, a majority of seed within the range of ca. 3±0.3 is of the first hybrid and a majority of seed within the range of ca. 4±0.2 is of the second hybrid. The purity of each sample is indicated by arrows representing the overall quantity of seeds and the quantity of respective hybrid seeds (see e.g., at the top right of FIG. 1B the indication of the relative proportions of hybrid seeds "1" and hybrid seeds "2" with respect to the overall quantity of seeds). It is noted that changing the range of the seed characteristic(s) from which the seed are taken provides control over the purity of the collected seed. Specific ranges of seed characteristic(s) may be selected to reach a required level of purity and a required mix between the hybrid types. The methods allow selecting and/or breeding specific parent varieties to yield empirical seed characteristic(s) distributions that enable separation of predefined types of hybrid seeds at predefined purity levels.

In general, in each application of the disclosed methods to a specific crop, both with respect to breeding the parent varieties and with respect to selecting the actual parents, considerations such as the separations among the distributions of the parents and the hybrids, as well as the degree of purity that each achievable by selecting certain portions of the overall distribution, i.e., the portion selected from the overall crop that is collected in the field (including a mix of parent and hybrid seeds) may be made anew to accommodate the disclosed method to the specific crop at hand. For example, depending on the technical separation capabilities, parent varieties may be selected to have their distribution means apart by 0.5, 1, 1.5 etc. times the sum of the respective standard deviations; hybrids may be selected to be separable from each other by having their distribution means apart by 0.2, 0.5, 1 etc. times the sum of the respective standard deviations; and hybrids may be selected to be separable from the parents (on each side) by having their distribution means apart by 0.2, 0.5, 1 etc. times the sum of the respective standard deviations. It is noted that as crops are usually bred toward a maximal value of additive seed characteristics such as seed size and seed weight, one of the parent crop varieties with the lower seed characteristic can usually be easily found. It is emphasized that while common breeding practices aim at similar and maximal additive seed characteristics, the present invention surprisingly selects or breeds one of the parent varieties to have a smaller seed characteristic to enable separation of the hybrids by this characteristic, compensating for the somewhat reduced seed characteristic by the enhanced the ability to separate one or both hybrids, a feature which is not known in the prior art (see discussion below).

These aspects are indicated schematically in FIGS. 1A, 1B by the arrows marking the separations between the respective distribution mean values and the corresponding standard variation (SD, indicated only for the parent varieties); and by the arrow marking the selection and respective purity of one types of seeds in the selection—$SEL_1$ and $SEL_2$ indicate possible selected portions of hybrid seeds 1 and 2 respectively, with corresponding levels of purity. In case a higher level of purity is required, parent distributions which are more narrow and/or more removed from the hybrid distributions may be bred and/or selected, and/or a smaller portion of seed (from the corresponding location in the cumulative distribution) may be selected. In case a lower level of purity is required the criteria outlined above may be relaxed.

In cases of real crops, parent varieties may be selected to exhibit distributions which allow hybrid seed separation by the seed characteristic(s), such as seed size, weight or color. It is noted that such selection is challenging and unexpected, as normally parent varieties are selected to have similar distributions of seed characteristics in order to yield uniform hybrids. In certain embodiments, parent varieties may be bred to yield hybrid seeds with required properties as well as to have differing distributions with respect to one or more seed characteristic which is intended to be used for separating the hybrid seed.

Figure 2:
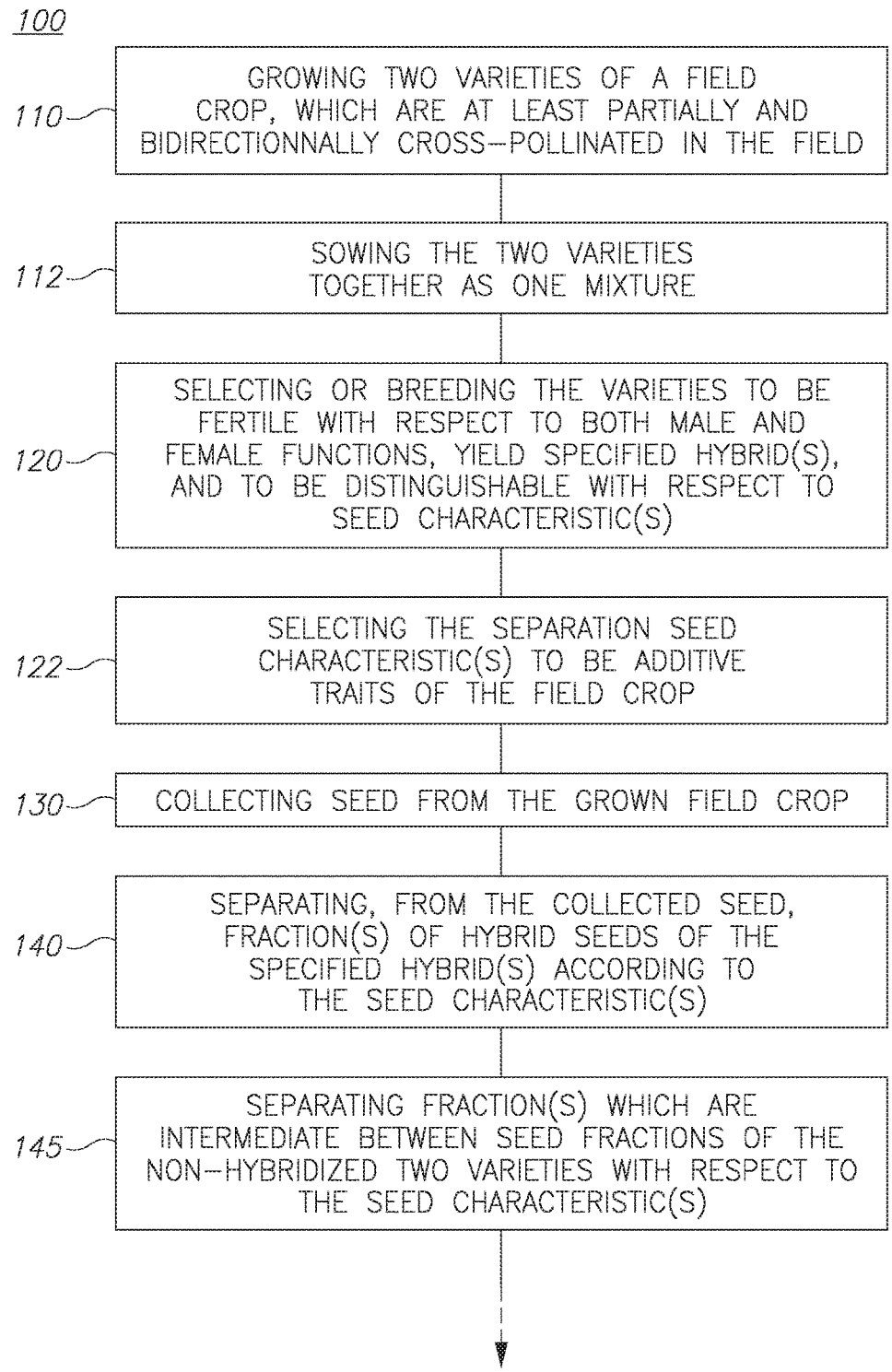
FIGS. 2 and 3 are high-level schematic flowcharts illustrating a method, according to some embodiments of the invention.
Figure 3:
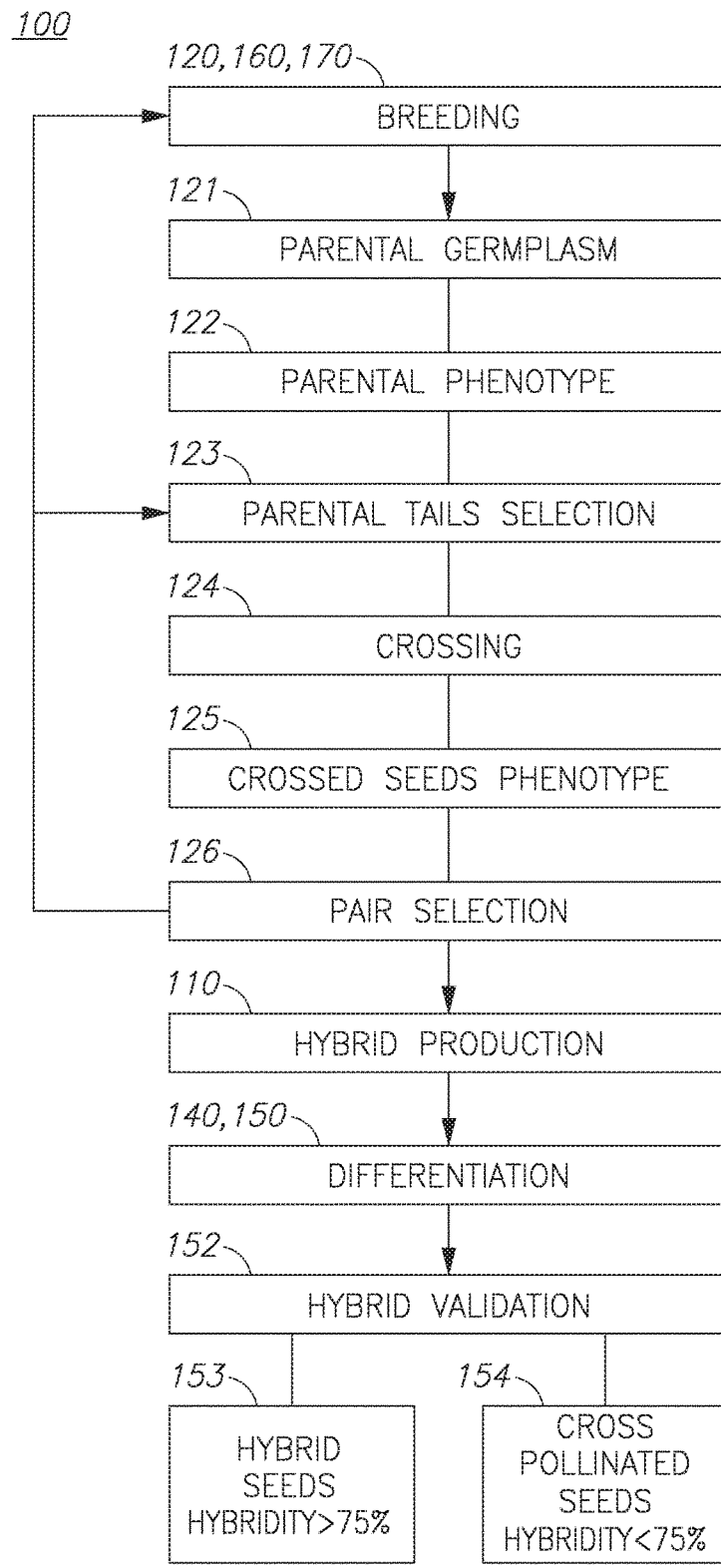

FIGS. 2 and 3 are high-level schematic flowcharts illustrating a method 100, according to some embodiments of the invention. Method 100 may comprise growing two varieties of a field crop which is at least partially cross-pollinated in the field (stage 110) i.e., the varieties are at least partially and bi-directionally cross pollinated in the field, e.g., by sowing the two varieties together as one mixture (stage 112), after selecting or breeding the varieties to be fertile with respect to both male and female functions, yield specified hybrid(s), and to be distinguishable with respect to seed characteristic(s) (stage 120). Method 100 may further comprise selecting the separation seed characteristic(s) to be additive traits of the field crop (stage 128).

Method 100 may further comprise collecting seed from the grown field crop (stage 130) and separating, from the collected seed, fraction(s) of hybrid seeds of the specified hybrid(s) according to the seed characteristic(s) (stage 140), for example, separating fraction(s) which are intermediate between seed fractions of the non-hybridized two varieties with respect to the seed characteristic(s) (stage 145).

Separation 140 and/or 145 may be carried out by various machines, and according to different seed characteristics. For example, seed shape may be used as seed characteristic by applying to the harvested seed a spiral separator, which uses gravity and centripetal force to separate rounder shaped seeds from flatter seeds. In another example, seed size may be used as seed characteristic by applying to the harvested seed an indented cylinder, configured to separate larger seeds from smaller seeds. In another example, seed weight may be used as seed characteristic by applying to the harvested seed a gravity table, which uses both air and gravity to separate the heavier seed from the lighter seed. In another example, internal seed components or compounds may be used as seed characteristic by applying to the harvested seed NIR (near infrared) spectroscopy technology or other spectroscopy-based technologies for separating the seeds based on specific signals which are linked to the internal components or compounds. Other seed characteristics as well as combinations of seed characteristics may be used to separate the hybrid seeds from the parent seeds and possibly from each other.

In certain embodiments, separation may be carried out in two stages. A first separation may be carried out between seed fractions (i) of one parent variety and a close hybrid on the one hand and (ii) of the second parent and a close hybrid on the other hand (referring as an example to FIGS. 1A, 1B—the first separation is between $1^{st}$ parent+$1^{st}$ hybrid on one hand and $2^{nd}$ parent+$2^{nd}$ hybrid on the other hand). A second separation may be then carried out within each (or at least one) group, i.e., between parent seeds and hybrid seeds in each group (referring as an example to FIGS. 1A, 1B—the second separation is between $1^{st}$ parent and $1^{st}$ hybrid in the first group, and between $2^{nd}$ parent and $2^{nd}$ hybrid in the second group). Different seed characteristics may be used in the first and second separations, e.g., seed color (as a maternal characteristic) may be used in the first separation while seed size or weight may be used for second separation. Advantageously, using a maternal characteristic may enable efficient separation between hybrids 1 and 2 as they result from different parent combinations (see Table 1). Seed color may be used as seed characteristic by applying to the harvested seed a color sorter in which an electronic eye adjusted to identify color differences is used to separate seeds having different colors. In certain embodiments, only hybrid 1 or only hybrid 2 may be separated, e.g., if maternal or paternal hybrids are preferred (respectively). In this case sowing proportions of the parent varieties may deviate from 1:1 in order to enhance the fraction of one type of hybrid seed over the other.

In certain embodiments, method 100 may comprise separating seed fractions according to maternal trait(s) and then separating parent and hybrid seeds in one or both fractions according to the (additive) seed characteristic(s) 150.

In certain embodiments, method 100 may further comprise breeding (or selecting) the variety(ies) to have mean values of the seed characteristic(s) of the non-hybridized two varieties which are separated by at least a sum of the standard deviations of the seed characteristic(s) of the non-hybridized two varieties (stage 160). Such separation of the distributions of the seed characteristic(s) may ensure the ability to separate the hybrid seed from the (pure) parent seeds efficiently.

In certain embodiments, method 100 may further comprise breeding (or selecting) the variety(ies) to yield a separation of the mean value of the seed characteristic(s) of the specified hybrid(s) from the closest non-hybridized variety which is at least a sum of the standard deviations thereof (stage 170). Such separation of the distributions of the seed characteristic(s) may ensure the ability to separate the hybrid seed from the (pure) parent seeds efficiently.

In certain embodiments, method 100 may further comprise selecting the two varieties to yield at least two specified hybrids, one from pollination of a first variety by a second variety and a second from pollination of the second variety by the first variety (stage 180). By selection and/or breeding of the parent varieties, the mean values of the at least one seed characteristic of the first and second seed fractions (of the corresponding first and second varieties) may be separated by at least a sum of the standard deviations of the at least one seed characteristic of the two hybrids. Separation of the hybrid seed according to seed characteristic(s) may be enabled by the different donations by the male parent and by the female parent to the seed characteristic(s) (see FIG. 7), for example, in cases maternal contribution to seed weight characteristic is larger than paternal contribution thereto, the direction of pollination may determine and enable the separation between the weights of the two hybrids (the lighter hybrid originating from maternal contribution of the lighter parent variety and the heavier hybrid originating from maternal contribution of the heavier parent variety). In certain embodiments, pollination characteristics may be manipulated or selected to favor the formation of one hybrid over the other, e.g., to simplify separation or increase separation efficiency. For example, wind pollinated crops may be grown with one of the parents upwind (when such conditions prevail in the growing region) and thus influence the relative frequency of the hybrids.

Certain embodiments comprise hybrid seed of two varieties of a field crop which is at least partially bi-directionally cross-pollinated in the field, wherein the two varieties are fertile with respect to both male and female functions, are selected to yield at least the hybrid seed, and are distinguishable with respect to at least one seed characteristic, wherein the mean values of the at least one seed characteristic of the non-hybridized two varieties are separated by at least a sum of the standard deviations of the at least one seed characteristic of the non-hybridized two varieties, and the hybrid seed are intermediate, with respect to the at least one seed characteristic, between seed of the non-hybridized two varieties. For example, the two varieties may be sown together as one mixture.

FIG. 3 schematically illustrates breeding steps as part of the realization of method 100, according to some embodiments of the invention.

Breeding the parental lines (stage 120, also stages 160, 170) may be carried out to achieve a wide genetic diversity which contains the product definition traits and diversity in seed characteristics such as: shape, size, weight, color and internal seed components (enzymes, nutrition, protein and metabolites). For one or more seed characteristics which are defined in advance as the "differentiation characteristic" (DC), breeding 120 may be conceived to set a wide variation of the DC for the ongoing process, which may be characterized in the parental germplasm 121. Parental phenotype 122 may be measured in several repetitions and for each parental line; for example, the mean value and standard deviation (SD) of the respective distributions may be calculated. Parental tails selection 123, referring to the tails of the distribution, may be carried out e.g., for the lines with the lower and upper 10% of the DC values (see example in Table 2 and FIG. 5 below).

Figure 4:
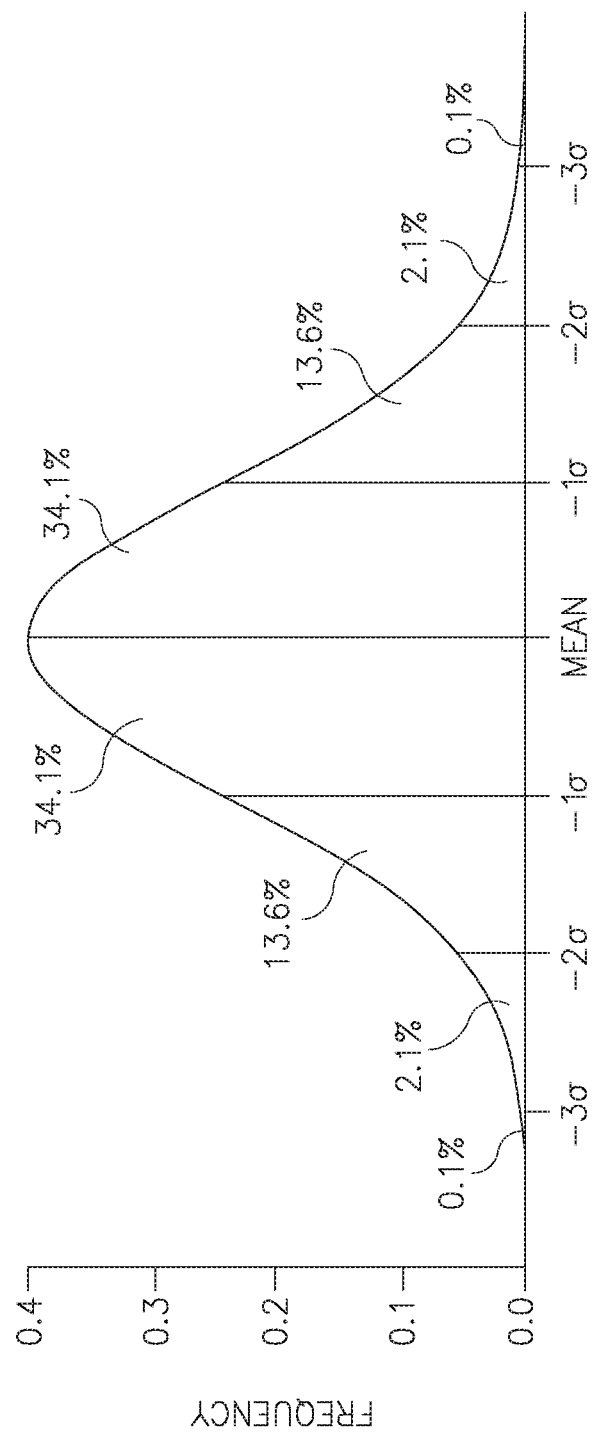
FIG. 4 illustrates the normal distribution with a notation of population sizes within on, two and three standard deviations ($\tau$).

FIG. 4 illustrates the normal distribution with a notation of population sizes within one, two and three standard deviations (a). As illustrated in FIG. 4, 68.2% of the population resides within $\pm 1\sigma$, 95.6% of the population resides within $\pm 2\sigma$ and 98.8% of the population resides within $\pm 3\sigma$. This is the basic distribution form expected for seed characteristics, as illustrated above in FIGS. 1A and 1B.

In case the seed characteristic (termed also differentiation characteristic (DC) above) is a normally distributed characteristic (i.e. having a distribution as in FIG. 4), this characteristic may be used to separate hybrid seeds according to a required purity criterion. For example, to be considered a pure hybrid lot according to the definition in Federal rules 7 CFR 201.11a—Hybrid and 7 CFR 201.26—Kind, variety, and hybrid, the separation may be configured to attain 95% purity of the separated hybrid seed. In another example, a mixed hybrid lot, defined as having between 75-95% hybrid seeds, may be separated by selecting the seeds within $\pm 1.15\sigma$ from the distribution mean value. It is noted that in case the seed characteristic has any specified distribution, corresponding definitions may be applied in the separation step to yield a required level of purity.

In certain embodiments, the following steps may be taken to implement breeding 120 in method 100. In N Parents, each with X weight measurements, the mean value and standard deviation of the seed characteristic are calculated. Some of the N parents are then selected into two groups with respect to the seed characteristic (e.g., big seeds and small seeds). For example, a certain distance from the overall average of the N parents may be selected as a threshold for inclusion in the two groups (see FIG. 5 below). Several parent are selected from each group according to seed characteristics and possibly statistical measures (e.g., three biggest from the big seeds group and three smallest from the small seeds group; or extreme parents with small standard deviations with respect to other extreme parents in each group). Hybrids from crossings of the selected parents are then evaluated according to their required traits, seed characteristics, and statistical measures of these parameters to identify hybrids with required traits, and (possibly narrow) distributions of seed characteristics which are distinct from the distributions of the seed characteristics of the parents. Selected hybrids and possibly parents may be used for further breeding 120 until required traits and seed characteristics are reached, the parents of the respective hybrids are then used for growing the hybrid seeds in production.

Figure 5:
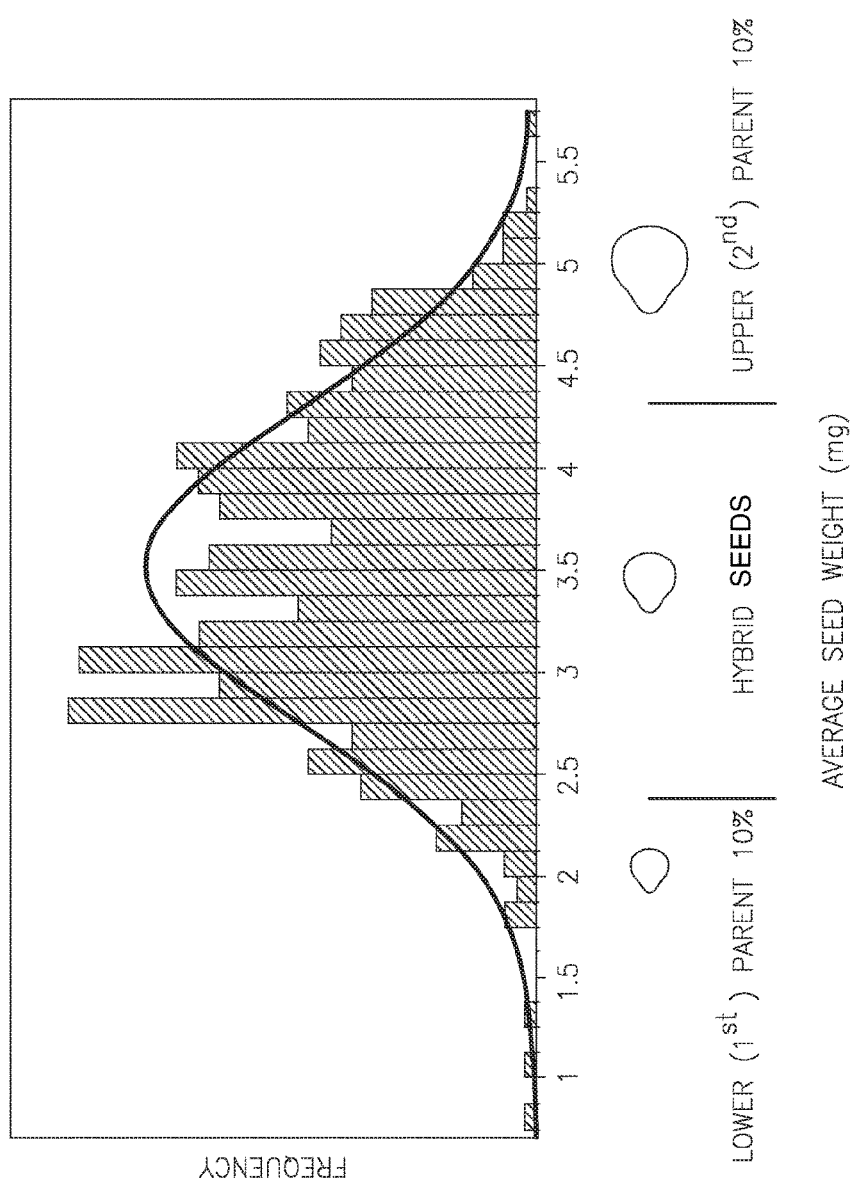
FIG. 5 illustrates an exemplary seed distribution with respect to the seed characteristic seed weight, in sesame.

Table 2 and FIG. 5 illustrate an exemplary seed distribution with respect to the seed characteristic seed weight, in sesame. Mean seed weights are for respective fractions. In FIG. 5 seed size in shown schematically as small, medium and large for the distribution tails and the central distribution region. The data represent 420 parental lines, the curve is a fitted normal distribution curve.

TABLE 2

An exemplary lines distribution with respect to the seed characteristic seed weight, in sesame. Mean seed weights are for respective fractions.

| Distribution | Mean seed weight (mg) | Distribution |
|---|---|---|
| 100.00% | 5.66 | |
| 99.50% | 5.2464 | |
| 97.50% | 4.892 | |
| 90.00% | 4.548 | 10% upper tail |
| 75.00% | 4.06 | |
| 50.00% | 3.46 | Mean value |
| 25.00% | 2.91 | |
| 10.00% | 2.59 | 10% lower tail |
| 2.50% | 2.178 | |
| 0.50% | 1.24 | |
| 0.00% | 0.83 | |

Parent selection or breeding 120 may aim at modifying the seed characteristic distribution across the crop to enable effective separation of the required hybrid seed.

Crop lines with SD higher than the average SD may be dropped out to achieve increased stability of the trait performance (the trait being different from the seed characteristics, and set as a performance requirement from the hybrid seeds or plants grown therefrom). In case of low diversity in the measured characteristic, breeding 120 may be intensified and conducted to introduce new diversity or even change the DC. For example, manually reciprocal crossing 124 between the selected parental lines may be carried out as a preliminary stage to yield the parental varieties to be grown, as exemplified in FIG. 8, below. Crossing 124 may e.g., comprise recurring crossing after determining crossed seeds phenotypes 125 (with respect to the aims of breeding 120) and selecting specific pairs for further crossing 126.

FIG. 8 exemplifies in a non-limiting manner the comparison of different parents as varieties for hybridization, with respect to the resulting distribution parameters, in sesame. In certain embodiments, FIG. 8 illustrates an example that may serve as a basis for a crossing stage (124-126) in the breeding of sesame parental lines to yield a hybrid variety. Six repetitions of each line are been measured to calculate mean value and SD (not shown). Parents 1-10 are shown, the average thousand seed weight (TGW; in gram) shown for each combination, together with the mean values and standard deviations for each combination.

The data in FIG. 8 allows the selection of a parental combination for a subsequent crossing 124, showing a large spread between the parents and between the hybrids in some of the cases. The breeding of the potential parent varieties may be reiterated to enhance the required distances in seed characteristics.

In certain examples, e.g., that of the crosses between P1 and P10, the crosses yield mean values which are well apart from the mean values of each of P1 and P10: the mean values of the seed characteristic of the non-hybridized two varieties (5.20±0.10 for P1 and 1.96±0.04 for P10) are separated by at least a sum of the standard deviations of the at least one seed characteristic of the non-hybridized two varieties (5.20−1.96=3.24>>0.10+0.04=0.14). Moreover, the mean values of the seed characteristic of each of the two hybrids—P1 as female P10 as male (3.50±0.05) and P1 as male P10 as female (3.15±0.40)—are separated from the closest one of the non-hybridized two varieties by at least the sum of the respective standard deviations (From P1: 5.20−3.50=1.70>> 0.10+0.05=0.15; From P10: 3.15−1.96=1.19>>0.04+0.40=0.44).

In other examples, e.g., that of crosses between P5 and P6, not only do the above conditions apply (P5: 4.95±0.04; P6: 2.19±0.04; P5 female and P6 male: 3.20±0.15; P6 female and P5 male: 4.05±0.08), but the mean values of the seed characteristic of the two hybrids are also separated by the sum of the respective standard deviations (4.05−3.20=0.85>0.15+0.08=0.23) providing easy separation and high purity of each of the hybrids as well. Such examples in FIG. 8 are shown in bold typeface.

It is also noted that in case of a heterotic trait, a combination between two parental lines with similar values (low or high) in a certain trait can result in a transgressive phenotype of the hybrid (for example the cross between P9 as female and P10 as male).

FIG. 8: An example for the crossing stage (124) in the breeding of parental lines for hybrid production in sesame. Ten lines were used to produce full reciprocal crossing matrix where each of the lines function as both female (x-axis) and male (y-axis) with all the other lines. Each square contains the results for a unique parental combination. At least six repetitions were measured for each combination and a mean Thousand Grain Weight (TGW; top number) and Standard Deviation (SD, a; bottom number in italic) were calculated. The results of the self-pollinations are presented in the diagonal square. In certain embodiments, a pair of parents showing the highest distance in the DC values of the hybrid seeds and the parental self-seeds may be selected 126 for further breeding or for hybrid production 110. In certain embodiments, a distance may be calculated by mean DC value and its SD between the hybrid seed lot and the self-seed lot using Equation 1 (using in this case, in a non-limiting manner the assumption that parent 1 shows a high DC value and parent 2 shows a low DC value):

(parent 1 DC value−SD)−(hybrid DC value+SD)=
    Upper differentiation value (hybrid DC value−SD)−(parent 2 DC value+SD)=
    Lower differentiation value          Equation 1:

It is noted that pair selection 126 may be used to change the starting parent pairs in order to achieve more favorable starting points with respect to the distribution parameters or with respect to the seed characteristic selected for separation.

The selected pair may contain the highest distance value, lower or upper compare to all measured crossing pairs. The distance between the seed lots increases differentiation (separation 140 and/or 145) efficiency. In case the distance value is lower than the separation machine limitation or even smaller than achieved before, crossing and selection 124-126 or generally breeding 120 may be reiterated until the required traits and seed characteristic(s) values are reached.

Table 4 provides a non-limiting list of prospective crops to be considered for application of certain embodiments. These crops exhibit a potential for seed differentiation as disclosed herein and were further selected according to their pollination mode (degree of cross pollination and pollination agent), seed characteristics (and ability to reach the disclosed separation) and commercial aspects to be appropriate candidates for application of the disclosed methods. It is noted that the crop species belong to a wide range of families with widely spread seed characteristics and pollination mechanisms (e.g., grasses, beet and buckwheat are wind pollinated while other crops are biotically pollinated). Initial experiments have validated the potential of certain embodiments in castor oil seed, sesame seed, maize, pepper and tomato, and ongoing experiments are carried out for validation in other crops.

TABLE 4

Exemplary list of candidate crops

| Species | Family name |
|---|---|
| Garlic, Onions | Amaryllidaceae |
| Carrots | Apiaceae |
| Sunflower seed | Asteraceae |
| Cabbage, Mustard seed, Rapeseed | Brassicaceae |
| Sugar beet | Chenopodiaceae |
| Cucumber, Melons, Pumpkins, Squash, Watermelons | Cucurbitaceae |
| Castor oil seed | Euphorbiaceae |
| Beans, Chick peas, Cloves, Groundnuts, Lentils, Lupins, Pea, Soybeans, Vetches | Faboideae |
| Cotton | Malvaceae |
| linseed | Linaceae |
| Sesame seed | Pedaliaceae |
| Barley, Maize, Rice (paddy), Rye, *Sorghum*, Triticale, Wheat | Poaceae |
| Buckwheat | Polygonaceae |
| Eggplants, Pepper, Potato, Tomato | Solanaceae |

Varieties of any of the following field crops may be selected and/or bred to yield parent varieties that provide the hybrid seeds as described herein: sesame, garlic, onion, carrot, sunflower, cabbage, mustard, rape, sugar beet, cucumber, melon, pumpkin, squash, watermelon, castor, bean, chick pea, clove, groundnut, lentil, lupine, pea, soybean, vetch, cotton, line, barley, maize, rice, rye, sorghum, triticale, wheat, buckwheat, eggplant, pepper, potato and tomato.

The effectivity of the disclosed methods depends on aspects such as the character of pollination patterns in the field (percentage of self vs. cross pollination), the typical variance in seed characteristics, especially those used for separation, availability of separation machinery, and economical considerations. For example, as explained above, crops having a large seed endosperm may provide hybrids which are more easily separated from each other than crops having a large embryo, while the latter may be more easily separated from the parent varieties. The selection of seed characteristic(s) for separation may vary among crop species. Of the crops listed above, the following crops may be differentiated on the basis of a large endosperm: Garlic, onion, sugar beet, castor oil seed, lineseed, sesame, the cereals (barley, maize, rice, rye, sorghum, triticale, wheat), and buckwheat; while the rest of the crops present a large embryo. Concerning the mode of pollination, the cereals, buckwheat and sugar beet are abiotically pollinated while the rest of the crops are biotically pollinated. Of the crops listed above, the method was validated by the inventor until the filing date in castor oil seed, sesame seed, maize, pepper and tomato, some of the relevant results are presented below (sesame was discussed above in detail, as a non-limiting example).

Table 5 illustrates the stability of seed weight as the seed characteristic, over multiple parents (top part of Table 5) and over different locations of the capsules on the parent plant (bottom part of Table 5) in sesame. The stability is important to enable a differentiation and consequently a separation between the variability of hybrid seeds from a given pair of parent types and the variability of hybrid seed from different types of parents. One of the criteria for selecting the specific parents may be the stability of the seed characteristic of their hybrids.

TABLE 5

Illustration of hybrid seed weight stability in sesame.

| Parent | repetition # | TGW(gr) | SD(gr) | % SD |
|---|---|---|---|---|
| P1 | 20 | 3.660 | 0.185 | 5% |
| P2 | 29 | 3.442 | 0.288 | 8% |
| P3 | 14 | 2.949 | 0.387 | 13% |
| P4 | 11 | 3.416 | 0.303 | 9% |
| P5 | 11 | 3.447 | 0.247 | 7% |
| P6 | 11 | 2.494 | 0.203 | 8% |
| P7 | 10 | 3.087 | 0.315 | 10% |
| P8 | 11 | 3.453 | 0.507 | 15% |
| P9 | 12 | 2.961 | 0.221 | 7% |
| P10 | 9 | 2.753 | 0.227 | 8% |
| P11 | 12 | 3.780 | 0.202 | 5% |
| P12 | 8 | 4.373 | 0.313 | 7% |
| Average | | | | 9% |

| Parent | location | repetition # | TGW(gr) | SD | % SD |
|---|---|---|---|---|---|
| P1 | Bottom-Middle | 14 | 3.631 | 0.199 | 5% |
| P1 | Middle | 6 | 3.727 | 0.139 | 4% |
| P2 | Bottom-Middle | 15 | 3.453 | 0.323 | 9% |
| P2 | Middle | 14 | 3.431 | 0.257 | 7% |

Table 6 exemplifies in a non-limiting manner the comparison of different parents as varieties for hybridization, with respect to the resulting distribution parameters, in pepper (analogous to FIG. 8). Table 6 illustrates an example that may serve as a basis for a crossing stage (124-126) in the breeding of pepper parental lines to yield a hybrid variety. It is noted that not all parent combinations yield viable seeds, a feature which is incorporated to the breeding process.

TABLE 6

An example for the crossing stage (124) in the breeding of parental lines for hybrid production in pepper.

| TGW(gr) SD(gr) | | | Male | | | | | | | | | | | |
|---|---|---|---|---|---|---|---|---|---|---|---|---|---|---|
| | | | P1 | P2 | P3 | P4 | P5 | P6 | P7 | P8 | P9 | P10 | P11 | P12 |
| Female | P1 | | 6.32 0.24 | | | | | | | | | | | |
| | P2 | | | 7.73 0.26 | | | | | | | | | | |
| | P3 | | | 4.27 0.06 | 8.23 0.03 | | | | | | | | | |

TABLE 6-continued

An example for the crossing stage (124) in the breeding of parental lines for hybrid production in pepper.

| TGW(gr) SD(gr) | | P1 | P2 | P3 | P4 | P5 | P6 | P7 | P8 | P9 | P10 | P11 | P12 |
|---|---|---|---|---|---|---|---|---|---|---|---|---|---|
| | P4 | | 3.50 | | 2.76 | | | | | | | | |
| | | | 0.03 | | 0.02 | | | | | | | | |
| | P5 | | 3.12 | | | 2.27 | | | | | | | |
| | | | 0.15 | | | 0.08 | | | | | | | |
| | P6 | | 2.87 | | | | 2.84 | | | | | | |
| | | | 0.10 | | | | 0.06 | | | | | | |
| | P7 | | 2.21 | | | | | 1.92 | | | | | |
| | | | 0.04 | | | | | 0.01 | | | | | |
| | P8 | | 5.08 | | | | | | 4.54 | | | | |
| | | | 0.05 | | | | | | 0.14 | | | | |
| | P9 | | 3.50 | | | | | | | 2.85 | | | |
| | | | 0.13 | | | | | | | 0.18 | | | |
| | P10 | | 5.43 | | | | | | | | 5.54 | | |
| | | | 0.12 | | | | | | | | 0.20 | | |
| | P11 | | 7.17 | | | | | | | | | 5.26 | |
| | | | 0.23 | | | | | | | | | 0.14 | |
| | P12 | 4.11 | 5.32 | | | | | | | | | | 5.29 |
| | | 0.01 | 0.02 | | | | | | | | | | 0.02 |

Table 7 exemplifies in a non-limiting manner an initial comparison of different parents as varieties for hybridization, with respect to the resulting distribution parameters, in tomato (analogous to FIG. 8). Table 7 illustrates an example that may serve as an initial basis for a crossing stage (124-126) in the breeding of tomato parental lines to yield a hybrid variety.

TABLE 7

An initial example for the crossing stage (124) in the breeding of parental lines for hybrid production in tomato.

| TGW(gr) SD(gr) | | Male | | |
|---|---|---|---|---|
| | | P1 | P2 | P3 |
| Female | P1 | 3.09 | | |
| | | 0.05 | | |
| | P2 | 2.15 | 0.71 | |
| | | 0.10 | 0.02 | |
| | P3 | 1.76 | | 0.65 |
| | | 0.09 | | 0.04 |

Figure 6:
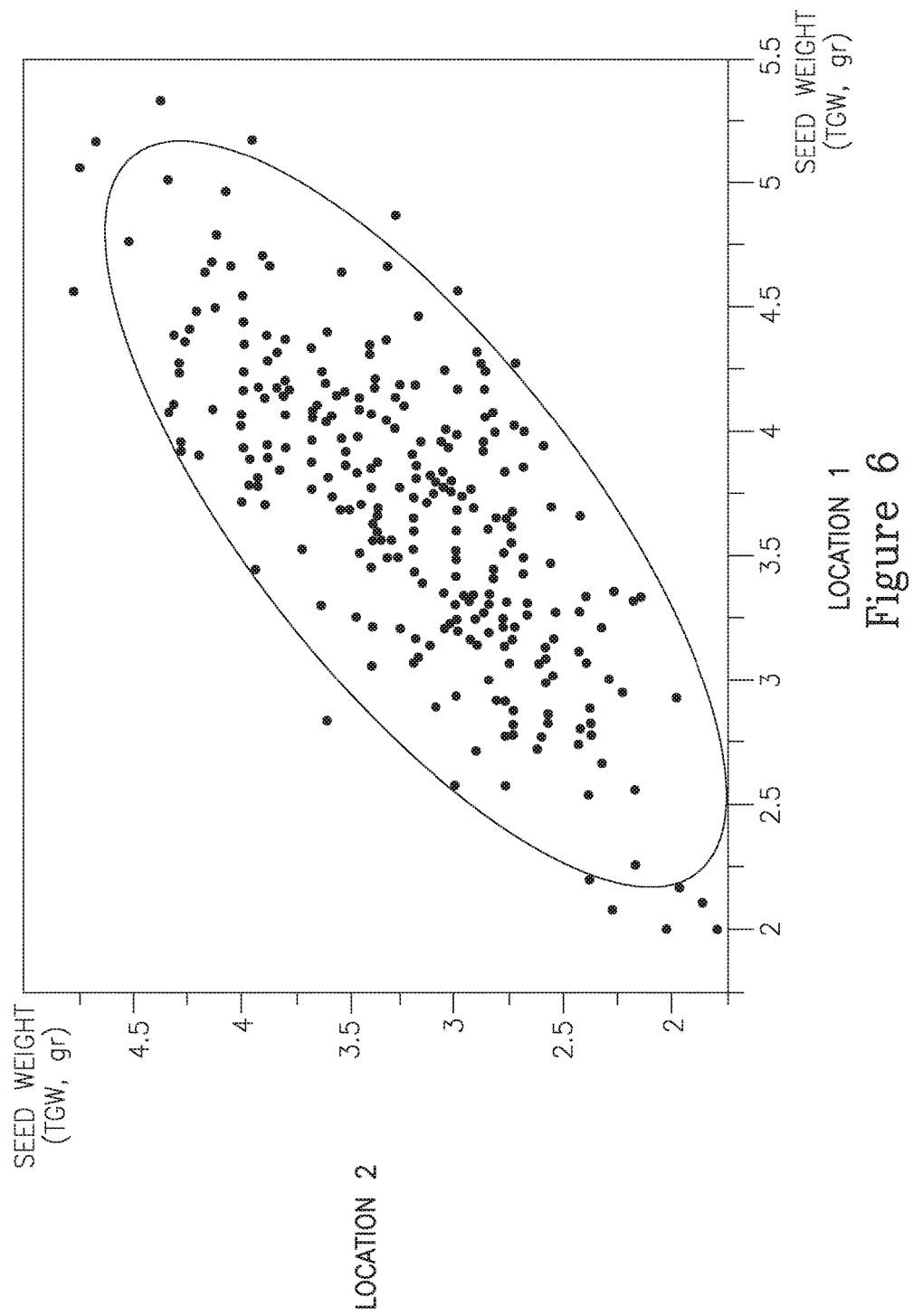
FIG. 6 exemplifies results from breeding at different locations, in the illustrated case, in different countries.

FIG. 6 exemplifies results from breeding at different locations, in the illustrated case, in different countries. The ellipse marks the good correlation between results in the two sites, which illustrates the stability of the hybrid seed characteristics at the different locations.

Hybrid production 110 may be based on natural pollination using biotic and/or abiotic vectors to produce hybrid seeds. The selected pairs of the parental lines may be sown in open field for pollination. In case of insect pollination, the field may be separated from other fields with compatible crops to avoid cross contamination. In case of abiotic pollination, the field may be separated according to parameters related to the pollination agent. For example in the case of wind pollination, the different pairs of parental lines can be separated with respect to the wind direction.

Method 100 may further comprise increasing cross pollination efficiency (stage 190) by any of the following means. In cases one parent variety is predominantly female and another parent variety is predominantly male (e.g., maternally affected traits), the parent varieties may be sown as a mixture to increase the efficacy of cross-pollination. In such cases, predominantly male varieties may be sown in larger proportion than predominantly female varieties to increase the availability of pollen and thus increase the cross-pollination proportion of the predominantly female variety. Predominantly female variety may be selected or bred to exhibit at least partial male sterility (genetic and/or induced) to increase the proportion of cross pollination seeds from the predominantly female plant (by reducing the number of self-seeds therefrom). Possibly, given sufficient cross-pollination, predominantly male and predominantly female varieties may be spatially separated and separately harvested to simplify separating the hybrid seeds from each harvest. Cross pollination may be enhanced and refined by applying biotic and abiotic factors such as introduction of bees or be attracting means, using artificial abiotic effects such as wind blowers, plant shakers etc. and locating the fields under consideration of bee behavior and propagation of abiotic pollination agents.

Method 100 may further comprise evaluation and validation of the hybrid seed lot (stage 152). For example, 1000 seeds may be selected after differentiation phase 140 and/or 145 and sown. The mature plants may be phenotyped and divided into three groups: first parent (e.g., predominantly female plants), second parent (e.g., predominantly male plants) and hybrids. The hybrid seeds lot may then be defined as "hybrid seeds" 153 if the percentage of hybridity is exceeding 75% or as "Cross pollinated seeds" 154 if the percentage of hybridity is below 75%. Clearly, any form of evaluation may be applied to confirm appropriate or required separation levels.

In a field experiment carried out in winter 2015, parent sesame plants were crossed to yield two varieties, one with smaller seeds than the other. Selection of seeds in the rage between 115% the smaller seed weight and 85% the larger seed weight were sown and all grown plants were found to be hybrid plant, supporting the proposed approach.

Advantageously, in contrast to U.S. Pat. Nos. 3,903,645 and 8,502,019, in the present invention pollen flow is free throughout the population and both varieties have functional male and female organs. Specifically, U.S. Pat. No. 3,903,645 teaches, in soybean, overcoming the natural self-pollination in soybean plants by using atypical soybean plants which do enable cross-pollination, resulting in different seed sizes from self- and cross-pollination, and spatially separating the varieties to enable collection of the hybrid seeds. Cross pollination in U.S. Pat. No. 3,903,645 is one-directional only, namely from the typical variety to the atypical variation, and does not involve separating the parent varieties with respect to an additive seed characteristic but with respect to floral morphology. U.S. Pat. No. 8,502,019 teaches, in alfalfa and soybean, using female (male sterile) plants pollinated by pollinizer plants which are highly self-incompatible, and spatially separating the varieties to enable collection of the hybrid seeds. Cross pollination in U.S. Pat. No. 8,502,019 is one-directional only, namely from the pollinizer plants to the female plants, and does not involve separating intermediate hybrid seeds as the female plants are incapable of self-pollination and the pollinizer plants are self-incompatible. In contrast, the disclosed parent varieties are fertile with respect to both male and female functions, and the invention still enables separation of the hybrid seeds under bi-directional pollination and mixed sowing in natural field conditions to required purity levels. Moreover, both U.S. Pat. Nos. 3,903,645 and 8,502,019 teach against the current invention as they teach designing the parent population to result in one-directional pollination only, by selecting partially sterile parent and by separating the parents in the field. These patents are specific to certain crops with certain floral characteristics and cannot be readily applied to other crops. Finally, these patents use abnormal parent forms which may yield inferior hybrid seeds due to genetic defect associated with the parent's anomaly. The current invention in contrast utilizes normally fertile parent varieties which may be selected according to required traits in their progeny.

Advantageously, in contrast to previous U.S. patents, describing methods for hybrid production or separation in which in all involve a certain level or type of male sterility plants, all the plants in the present invention have normal fertile flowers and no biological or mechanical barriers are required to assure one-directional pollination. In particular, the parent varieties are bred to control one or more additive characteristic of the hybrid seeds, which allows their separation into fraction after the seeds are ripe.

In the above description, an embodiment is an example or implementation of the invention. The various appearances of "one embodiment", "an embodiment", "certain embodiments" or "some embodiments" do not necessarily all refer to the same embodiments.

Although various features of the invention may be described in the context of a single embodiment, the features may also be provided separately or in any suitable combination. Conversely, although the invention may be described herein in the context of separate embodiments for clarity, the invention may also be implemented in a single embodiment.

Certain embodiments of the invention may include features from different embodiments disclosed above, and certain embodiments may incorporate elements from other embodiments disclosed above. The disclosure of elements of the invention in the context of a specific embodiment is not to be taken as limiting their used in the specific embodiment alone.

Furthermore, it is to be understood that the invention can be carried out or practiced in various ways and that the invention can be implemented in certain embodiments other than the ones outlined in the description above.

The invention is not limited to those diagrams or to the corresponding descriptions. For example, flow need not move through each illustrated box or state, or in exactly the same order as illustrated and described.

Meanings of technical and scientific terms used herein are to be commonly understood as by one of ordinary skill in the art to which the invention belongs, unless otherwise defined.

While the invention has been described with respect to a limited number of embodiments, these should not be construed as limitations on the scope of the invention, but rather as exemplifications of some of the preferred embodiments. Other possible variations, modifications, and applications are also within the scope of the invention. Accordingly, the scope of the invention should not be limited by what has thus far been described, but by the appended claims and their legal equivalents.

What is claimed is:

1. A method of obtaining specified hybrid seeds, the method comprising:
    growing two varieties of a field crop which are mixed and bi-directionally cross-pollinated in the field, wherein the two varieties:
        are fertile with respect to both male and female functions,
        are selected to yield at least one specified hybrid, and
        are distinguishable with respect to at least one seed characteristic relating to at least one respective additive trait, wherein the at least one seed characteristic is at least one of: seed shape, seed size, seed color, seed weight, and seed contents including amino acid, protein and/or oil content,
    collecting seeds from both varieties of the grown field crop, and
    separating, from the collected seeds, at least one fraction of hybrid seeds of the at least one specified hybrid, wherein the at least one separated fraction is intermediate, with respect to the at least one seed characteristic, between seed fractions of the non-hybridized two varieties,
    wherein a mean value of the at least one seed characteristic of the at least one specified hybrid is separated from a mean value of the at least one seed characteristic of a closest one of the non-hybridized two varieties by at least a sum of standard deviations of the at least one seed characteristic of the at least one specified hybrid and the closest non-hybridized variety,
    wherein the crop is not soybean.

2. The method of claim 1, further comprising sowing the two varieties together as one mixture.

3. The method of claim 1, wherein the mean values of the at least one seed characteristic of the non-hybridized two varieties are separated by at least a sum of the standard deviations of the at least one seed characteristic of the non-hybridized two varieties.

4. The method of claim 3, further comprising breeding at least one of the two varieties to yield a separation of the mean values of the at least one seed characteristic of the non-hybridized two varieties, wherein the separation of the mean values is at least a sum of the standard deviations of the at least one seed characteristic of the non-hybridized two varieties.

5. The method of claim 1, further comprising breeding at least one of the two varieties to yield a separation of the mean value of the at least one seed characteristic of the at least one specified hybrid from a mean value of the at least one seed characteristic of a closest one of the non-hybridized two varieties, wherein the separation of the mean values is at least a sum of the standard deviations of the at least one seed characteristic of the at least one specified hybrid and the closest non-hybridized variety.

6. The method of claim 1, wherein:
the two varieties are selected to yield at least two specified hybrids, a first hybrid resulting from pollination of a first variety by a second variety and a second hybrid resulting from pollination of the second variety by the first variety,
the at least one fraction comprises a first seed fraction of the first hybrid and a second seed fraction of the second hybrid, and
the mean values of the at least one seed characteristic of the first and second fractions are separated by at least a sum of the standard deviations of the at least one seed characteristic of the two hybrids.

7. The method of claim 6, further comprising breeding at least one of the two varieties to yield the separation of the mean values of the at least one seed characteristic of the first and second fractions by at least the sum of the standard deviations of the at least one seed characteristic of the two hybrids.

8. The method of claim 1, wherein the mean values and the standard deviations are statistical measures of empirical distributions of the respective seeds.

9. The method of claim 1, wherein the field crop is sesame.

10. The method of claim 1, wherein the field crop is one of: garlic, onion, carrot, sunflower, cabbage, mustard, rape, sugar beet, cucumber, melon, pumpkin, squash, watermelon, castor, bean, chick pea, clove, groundnut, lentil, lupine, pea, vetch, cotton, linseed, barley, maize, rice, rye, sorghum, triticale, wheat, buckwheat, eggplant, pepper, potato and tomato.

11. A method of obtaining specified hybrid seeds, the method comprising:
sowing, together as one mixture, two varieties of a field crop which are bi-directionally cross-pollinated in the field, wherein the two varieties:
are fertile with respect to both male and female functions,
are selected to yield at least one specified hybrid, and
are distinguishable with respect to at least one seed characteristic relating to at least one respective additive trait, wherein the at least one seed characteristic is at least one of: seed shape, seed size, seed color, seed weight, and seed contents including amino acid, protein and/or oil content,
collecting seeds from both varieties of the grown field crop, and
separating, from the collected seeds, at least one fraction of hybrid seeds of the at least one specified hybrid, wherein the at least one separated fraction is intermediate, with respect to the at least one seed characteristic, between seed fractions of the non-hybridized two varieties,
wherein a mean value of the at least one seed characteristic of the at least one specified hybrid is separated from a mean value of the at least one seed characteristic of a closest one of the non-hybridized two varieties by at least a sum of standard deviations of the at least one seed characteristic of the at least one specified hybrid and the closest non-hybridized variety,
wherein the crop is not soybean.

12. The method of claim 11, wherein the field crop is sesame.

* * * * *